US00PP16738P2

(12) United States Plant Patent
Gossett

(10) Patent No.: US PP16,738 P2
(45) Date of Patent: Jun. 27, 2006

(54) ***TIARELLA* PLANT NAMED 'SUGAR AND SPICE'**

(50) Latin Name: ***Tiarella* hybrid**
Varietal Denomination: Sugar and Spice

(75) Inventor: Gary J. Gossett, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 86 days.

(21) Appl. No.: 11/083,835

(22) Filed: Mar. 16, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
*Assistant Examiner*—June Hwu
(74) *Attorney, Agent, or Firm*—Klarquist Sparkman, LLP

(57) ABSTRACT

A new and distinct cultivar of *Tiarella* plant characterized by its medium size, mounding habit, pink to white flowers, and pinnately divided leaves with a broad dark band down each division.

1 Drawing Sheet

Botanical denomination: *Tiarella* hybrid.
Variety designation: 'Sugar and Spice'.

BACKGROUND OF THE INVENTION

The present invention relates to a new and distinct cultivar of a hardy herbaceous perennial of the genus *Tiarella*, and known by the cultivar name 'Sugar and Spice'. The genus *Tiarella* is a member of the family *Saxifragaceae*.

The new cultivar originated as a cross between unknown parents. This new *Tiarella* was one of many seedlings grown from select experimental and proprietary interspecific hybrids and species that were mass pollinated in the greenhouse in Canby, Oreg. From observation of the characteristics exhibited by the instant plant, it is probable that *Tiarella trifoliata* var. *laciniata* and *T. wherryi* are in its parentage.

SUMMARY OF THE INVENTION

This plant is characterized by the following:

1. Medium size.
2. Mounding habit.
3. Pinnately divided leaves with a broad dark band down each division.
4. Pink flower buds and white flower color.
5. Excellent vigor.

The new variety has been reproduced only by asexual propagation (division and micropropagation). Each of the progeny exhibits identical characteristics to the original plant. Asexual propagation by division and micropropagation using standard techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a two-year-old *Tiarella* 'Sugar and Spice' in bloom grown outside in a one gallon container in the garden in April in Canby, Oreg.

DETAILED PLANT DESCRIPTION

The following is a detailed description of the new *Tiarella* hybrid based on observations of two-year-old plants grown outside in a one gallon container in the open air with 50% shade cover and added irrigation in the summer months in Canby, Oreg. Canby is Zone 8 on the USDA Hardiness map. Temperatures range from a high of 95 degrees F. in August to an average low of 32 degrees F. in January. Normal rainfall in Canby is 42.8 inches per year. The color descriptions are all based on The Royal Horticultural Society Colour Chart.

Botanical classification: *Tiarella* hybrid.
Variety denomination: 'Sugar and Spice'.
Plant:
- *Type*.—Herbaceous perennial.
- *Hardiness*.—USDA Zones 4 to 9.
- *Form*.—Mounding.
- *Size*.—30 cm wide and 30 cm high from the soil to the top of the foliage.
- *Vigor*.—Excellent.
- *Roots*.—Fibrous, freely branching, fine, and white in color. Roots develop easily from crown divisions.

Foliage:
- *Type*.—Simple.
- *Arrangement*.—Rosette.
- *Shape*.—Ovate.
- *Lobing*.—Varies. 5 to 7 main lobes. Terminal lobe is the longest. It is ovate with two lateral lobes and is cut almost to the main vein.
- *Margins*.—Crenate.
- *Venation*.—Palmate.
- *Apex*.—Mucronulate.
- *Base*.—Cordate, sometimes overlapping slightly.
- *Blade length*.—6.5 to 8.2 cm.
- *Blade width*.—6 to 7 cm.

*Texture*.—Thin, rough.
*Surface*.—Hispid top and bottom, matte.
*Petiole length*.—10 to 12 cm.
*Petiole surface*.—Hirsute.
*Petiole color*.—Yellow Green 146B maturing to Greyed Orange 177A.
*Leaf color*.—Spring upper surface — Yellow Green 144A, with a dark pattern along the veins covering 50 percent of the leaf, Greyed Purple 183A. Summer upper surface — Glossy. Yellow Green 148A to 147B, sometimes with some Green 137B near the tip. The dark pattern is Brown 200A. Under surface — Yellow Green 146B.

Inflorescence:
*Type*.—Raceme.
*Flower number*.—30 to 50 per raceme.
*Bloom period*.—April to May with sporadic rebloom throughout the summer and fall.
*Peduncle*.—Unbranched with 1 or 2 leafy bracts. Height — Grows to 34 cm. Width — 2.5 mm at the widest point. Color — Yellow Green 146A to Brown 200C. Texture — Hispid.
*Pedicel*.—Length — 7 mm. Texture — Hispid. Color — Pink, Greyed Purple 186C.
*Lastingness*.—A raceme blooms for about 3 weeks.

Flower bud:
*Size*.—3 mm deep and 2 mm wide.
*Description*.—Ovoid, downfacing until open.
*Color*.—Pink, Red Purple 62C.

Flower:
*Type*.—Perfect, actinomorphic, sepals petaloid.
*Shape*.—Rotate.
*Flower size*.—9 mm wide and 6 mm deep including stamens and pistil.
*Petal number*.—5.
*Petal shape*.—Lanceolate with a clawed base, reflexs when mature.
*Petal size*.—5 mm long and 1 mm wide.
*Petal color*.—White 155D inside and outside.
*Calyx*.—5, petaloid, parted almost to the base, reflexed.
*Calyx color*.—White 155A inside and outside.
*Sepal*.—5 in number, lanceolate, lobes 4 mm long and 1.6 mm wide.
*Stamens*.—10, conspicuously exerted.
*Filaments*.—White 155D, 6 mm long.
*Anthers undehisced*.—Orange 29B.
*Pollen color*.—Orange 29A.
*Pistil*.—White 155A, 6 mm long.
*Fragrance*.—Sweet.

Fruit:
*Type*.—A one-celled capsule, beak-like, composed of two unequal parts.
*Size*.—0.7 cm long.
*Color*.—Brown 200C.

Seeds:
*Color*.—Black 202A.
*Shape*.—Minute, oval, 1 mm long.
*Fertility*.—Fertile.

Pest and disease resistance: This new hybrid shows good powdery mildew tolerance, the main problem for *Tiarella*. No major pest problems. It is susceptible to root weevils like all *Tiarella*.

COMPARISONS WITH SIMILAR *TIARELLA*

Compared with *Tiarella* 'Neon Lights' (U.S. Plant Pat. No. 13,289), *Tiarella* 'Sugar and Spice' has similar leaf shape and size except that 'Neon Lights' has more secondary lobing. The leaves of 'Sugar and Spice' are darker with more olive tones on the mature leaves. The flowers on this new cultivar are more numerous, pinker, and have stronger, shorter stems.

I claim:

1. A new and distinct cultivar of *Tiarella* plant herein illustrated and described.

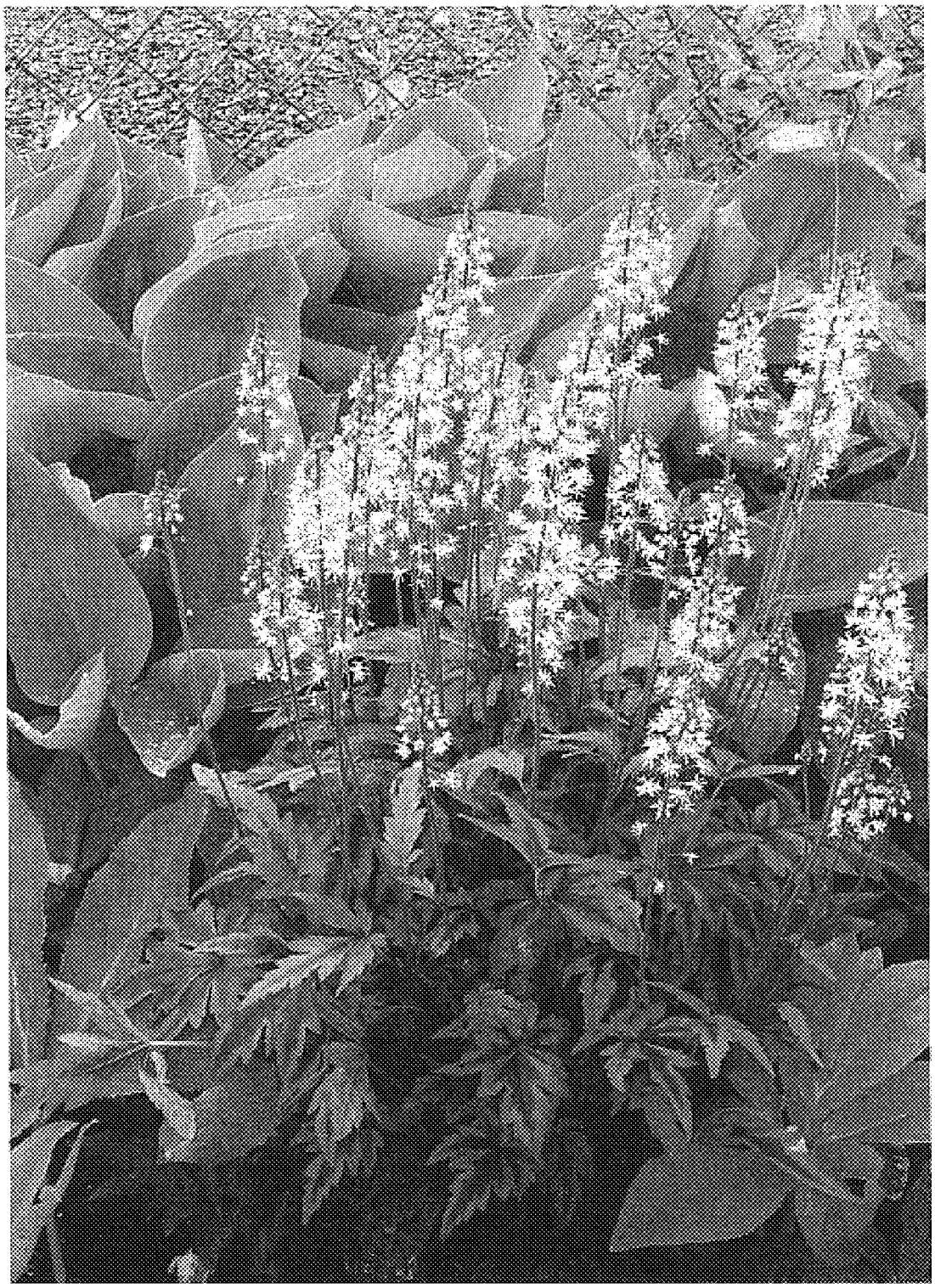

* * * * *